United States Patent [19]

Shively

[11] Patent Number: 5,407,683
[45] Date of Patent: Apr. 18, 1995

[54] PHARMACEUTICAL SOLUTIONS AND EMULSIONS CONTAINING TAXOL

[75] Inventor: Merrick L. Shively, Louisville, Colo.

[73] Assignee: Research Corporation Technologies, Inc., Tucson, Ariz.

[21] Appl. No.: 955,282

[22] Filed: Oct. 1, 1992

Related U.S. Application Data

[63] Continuation-in-part of Ser. No. 830,058, Feb. 3, 1992, abandoned, which is a continuation-in-part of Ser. No. 531,847, Jun. 1, 1990, abandoned.

[51] Int. Cl.$^6$ .................. A01N 65/00; C07D 305/00
[52] U.S. Cl. .................................. 424/439; 549/510; 424/195.1; 424/523
[58] Field of Search ............... 424/195.1, 520, 523, 424/485, 484, 486, 439, 440, 409

[56] References Cited

U.S. PATENT DOCUMENTS

| | | | |
|---|---|---|---|
| 3,723,134 | 3/1973 | Chivers | 99/134 |
| 5,011,532 | 4/1991 | Fuisz | 106/215 |
| 5,032,400 | 7/1991 | Wiersum et al. | 424/195.1 |

OTHER PUBLICATIONS

*Chemical Abstracts* 107(5):34441n.
Russel et al. (1987) "Intratesticular Injection as a Method to Assess the Potential Toxicity of Various Agents and Study Mechanisms of Normal Spermatogenesis" *Gamete Research* 17(1): 43–56.
Tarr et al. (1987) *Pharm. Res.* 4:162–165.
Horwitz (1992) *TIPS* 13:134–136.
Rowinsky et al. (1990) *J. Natl. Cancer Inst.* 82:1247–1259.
Grem et al. (1987) *Cancer Treat. Rep.* 71:1179–1184.

*Primary Examiner*—Thurman K. Page
*Assistant Examiner*—Peter F. Kulkosky
*Attorney, Agent, or Firm*—Greenlee and Winner

[57] ABSTRACT

Compositions of matter are provided comprising a pharmaceutically effective amount of taxol or a tumor-active analog thereof solubilized in a pharmaceutically acceptable carrier comprising an oil having a dipole moment of between about 0.5 Debyes and about 2.0 Debyes, and preferably between about 1.6 and about 1.7 Debyes. Oils from marine organisms having an ether lipid as a major component thereof are preferred. Methods of solubilizing taxol or tumor-active taxol analogs in the pharmaceutically acceptable oils of this invention are provided comprising forming a first solution by dissolving taxol in a preliminary solvent such as an anhydrous alcohol, then adding sufficient oil to solubilize said first solution. Taxol-in-oil solutions are used to prepare oil-in-water emulsions for pharmaceutical use in anti-tumor therapy by means known to the art using known surfactants. Self-emulsifying glasses comprising taxol or tumor-active taxol analogs are also provided comprising a water-soluble, nonsurface active matrix compound and taxol-oil solutions. Emulsions are readily formed from such glasses by contacting the glass with an aqueous phase.

8 Claims, No Drawings

PHARMACEUTICAL SOLUTIONS AND EMULSIONS CONTAINING TAXOL

This application is a C-I-P of Ser. No. 07/830,058, filed Feb. 3, 1992, which is a C-I-P of Ser. No. 07/531,847, filed Jun. 1, 1990, both now abandoned.

FIELD OF THE INVENTION

This invention is in the field of pharmaceutical compositions, specifically compositions containing the anticancer drug, taxol.

CROSS-REFERENCE TO RELATED APPLICATIONS

This application is a continuation-in-part of U.S. patent application Ser. No. 07/830,058, filed Feb. 3, 1992, now abandoned, incorporated in its entirety by reference herein, which is a continuation-in-part of U.S. patent application Ser. No. 07/531,847, filed Jun. 1, 1990, also incorporated in its entirety by reference herein. Said Ser. No. 07/531,847 is a continuation of International Patent Application PCT 91/03864, filed May 31, 1991, and Applicant claims benefit of the filing date of that application. PCT 91/03864 is incorporated in its entirety by reference herein. This application also incorporates by reference U.S. patent application Ser. No. 07/954,817, filed Oct. 1, 1992, which is a continuation-in-part of U.S. patent application Ser. No. 07/830,058, now abandoned

BACKGROUND OF THE INVENTION

Taxol is a poorly water soluble alkaloid isolated from several species of Western Yew. Taxol exhibits antimitotic properties and is presently undergoing phase I clinical trials for the treatment of cancers. Taxol has been shown to be active against leukemia, colon, breast, melanoma, sarcomas, and Lewis lung tumor systems. Tarr et al. (1987) Pharm. Res. 4:162-165; Horwitz (1992) TIPS 13:134-131. In vitro studies indicate that concentrations of taxol (0.1-10.0 μg/ml, stabilize microtubules, thus disrupting normal cell division. Rowinsky et al. (1990) J. Natl. Cancer Inst. 82:1247-1259.

Taxol is a complex diterpene having a taxane ring system with a four-membered oxetane ring and an ester sidechain at position C-13, as follows:

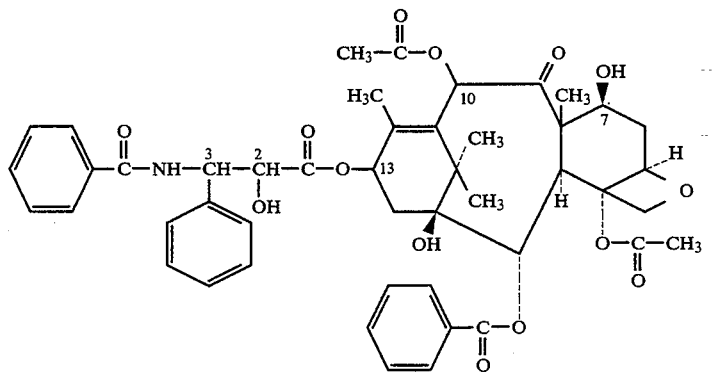

compounds that retain activity. Rowinsky et al. (1990) J. Natl. Cancer Inst. 82:1247-1259.

Because of its poor solubility in water and many oils, taxol has been administered in formulations using cremophors. Cremophors are polyoxyethylated castor oils. The current Sigma taxol formulation most widely used consists of ethanol:cremophor EL:isotonic saline (5:5:90). The drug's solubility in this vehicle does not exceed 0.6 mg/ml and it remains physically stable only for a short time (3 hr). Therefore, large volumes of these formulations, with limited solubility, would have to be infused to obtain a desired total dose of 30 mg. Tarr et al. (1987) Pharm. Res. 4:162-165. The patient is usually required to check into a hospital and endure intravenous infusion for an extended period, such as twenty-four hours. Typically, taxol is administered intravenously in a preparation containing 30 μg/ml over a period of twenty-four hours, followed by a week of rest and another dose. This is repeated two more times.

Further, the BASF cremophor EL (polyoxyethylated castor oil), is extremely toxic and has been shown to produced vasodilation, labored breathing, lethargy, hypotension and death in dogs. Rowinsky et al. (1990) J. Natl. Cancer Inst. 82:1247-1259. Anaphylactoid reactions attributed to the cremophor have also been observed. Green et al. (1987) Cancer Treat. Rep. 71:1179-1184.

Hypersensitivity reactions have been observed using the above formulation; one patient had a fatal reaction. It is unclear whether taxol itself or its cremophor vehicle is principally responsible for the hypersensitivity reactions. Rowinsky et al. (1990) J. Natl. Cancer Inst. 82:1247-1259.

Cosolvents have also been utilized in taxol preparations but require infusion times even longer than the currently-used formulation. Drugs with cosolvent formulations may precipitate if infused too fast.

In an attempt to overcome the taxol formulation problems using the toxic cremophor, and in an attempt to provide a formulation from which the active ingredient would not precipitate out from the aqueous solvent after IV administration, Tarr et al. (1987) Pharm. Res. 4:162-165, attempted to formulate taxol with Intralipid (trademark of RabiVitrum (formerly Cutter Medical) comprising soybean oil, lecithin, egg yolk phospholipids, and glycerol), a commonly used parenteral emulsion; however, the poor solubility of taxol in soybean oil (0.3 mg/ml) made this vehicle unsuitable.

In an attempt to increase taxol's solubility and develop more feasible clinical formulations, investigators have acylated carbons of taxol's taxene ring at the 7-position and 10-position. These efforts have yielded Tarr et al. then made taxol emulsion formulations using triacetin, in which the solubility of taxol is 30 mg/ml, along with emulsifying agents L-alpha-lecithin, pluronic F-86 of BASF company, polysorbate 80 of Sigma Chemical Co., and ethyl oleate. Glyercol was also added to slow creaming. Toxicity of the formulation was observed, including lethargy, ataxia and respiratory depression in animal models, presumably due to the toxicity of the triacetin. The emulsion showed an intravenous LD50 of 1.3 ml/kg in mice. The tricetin emulsion initially gave a 1 μm average diameter droplet and exhibited instability, separating into two phases at six months. Vigorous shaking again formed an emulsion having an average droplet size of 2 micrometers.

As taxol has been determined to be an especially effective anti-cancer agent, formulations which do not contain toxic ingredients and which allow delivery of pharmaceutically relevant dosages in a reasonable period of time, such as orally or by injection, are especially needed. Such formulations have not been previously available.

Methods and compositions for solubilizing pharmaceutically relevant dosages of taxol in pharmaceutically acceptable oils are therefore highly desirable objects of this invention.

The use of oil-in-water emulsions for delivery of taxol and its active analogs are needed to avoid problems of precipitation of I.V. solutions at the time of administration, increase bioavailability of orally administered taxol and prevent gastrointestinal upset. In nonemulsified form, taxol is degraded in the stomach. However, prior efforts to produce pharmaceutically-acceptable emulsions containing the taxol have failed due both to the relative insolubility of taxol in typical pharmaceutically suitable oils and due to the need for the use of toxic surface-active agents.

U.S. application Ser. No. 07/830,058 which is incorporated herein by reference, provides novel methods and compositions for forming pharmaceutical emulsions without using conventional surfactants. The use of these novel emulsification methods and compositions in combination with the novel solutions of taxol and its active analogs provided herein are objects of this invention.

Pharmaceutically acceptable oils useful in forming oil-in-water emulsions are well-known to the art and include vegetable, animal and marine oils. However, the poor solubility of taxol in most oils, such as safflower, olive and soybean oil (about 0.3–0.6 mg/ml), has prevented the use of such oils in previously-known taxol formulations.

Marine oils, especially those that are classified as ether lipids as opposed to triglycerides, are known to the art and include orange roughy, squalane, squalene and shark liver oil.

SUMMARY OF THE INVENTION

This invention provides compositions of matter comprising a pharmaceutically effective amount of taxol or a tumor-active analog thereof solubilized in a pharmaceutically acceptable carrier comprising an oil having a dipole moment of between about 0.5 Debyes and about 2.0 Debyes, and preferably between about 1.6 and about 1.7 Debyes. Oils from deep-water marine organisms are preferred.

The compositions of the present invention show a many-fold increase (up to five hundred times) of oral absorption over the prior art formulation using the EL cremophor (Trademark of BASF).

Solutions of taxol or tumor-active taxol analogs in the pharmaceutically acceptable oils of this invention may be prepared by directly dissolving taxol in the oil or by forming a first solution by dissolving taxol in a preliminary solvent such as an anhydrous alcohol followed by mixing with the oil and evaporation of the solvent.

The solutions of taxol or tumor-active analogs of taxol made by the methods of this invention are preferably used to prepare oil-in-water emulsions for pharmaceutical use in anti-tumor therapy. Emulsions are preferred vehicles for taxol for both intravenous and oral administration, and can be prepared by means known to the art using known surfactants from the solutions of taxol in oils of this invention.

Oil-in-water emulsions containing taxol can also be made using self-emulsifying glasses prepared as disclosed in abandoned U.S. Ser. No. 07/830,058 and subsequent related applications. Such glass compositions comprise a water-soluble, nonsurface active matrix compound and an oil containing solubilized taxol from which emulsions can be readily formed by contacting the glass with an aqueous phase.

The oil-in-water emulsions produced from these self-emulsifying glasses do not require art-recognized surfactants or emulsifying agents. The matrix compounds are not surface active agents, surfactants or emulsifying agents. Among others, monosaccharides, disaccharides and nonsugar sweeteners such as cyclamates, saccharines and water soluble polymers including polyvinyl-pyrrolidones (PVP), cellulose derivatives, dextrans and maltodextrins function as matrix compounds in the formation of such self-emulsifying glasses.

A pharmaceutically effective emulsion containing taxol is produced from the self-emulsifying glass by mixing with sufficient aqueous phase, to form an emulsion. No emulsive mixing or surfactants are necessary.

Such emulsions are administered to patients suffering from cancers against which taxol is known to have a therapeutic effect in appropriate oral or intravenous dosages to effect reduction in the disease.

DETAILED DESCRIPTION OF THE PREFERRED EMBODIMENTS

A composition of matter is provided comprising a pharmaceutically effective amount of taxol or a tumor-active analog thereof solubilized in a pharmaceutically acceptable carrier comprising an oil having a dipole moment of between about 0.5 Debyes and about 2.0 Debyes, and preferably between about 1.6 and about 1.7 Debyes.

A pharmaceutically relevant dosage or pharmaceutically effective amount of taxol for humans is about 30 mg per dose, repeated several times at weekly intervals. At solubilities of taxol in present formulations and because of the toxicity of the cremophor used in the formulation, concentrations of only about 30 μg/ml are presently used to administer taxol, thus requiring a volume of 1,000 ml for a single dose. Concentrations of taxol in oil up to about 10 mg/ml are achievable through the use of this invention, thus allowing delivery of a pharmaceutically relevant dose in a significantly lower amount of the pharmaceutical preparation. The final emulsions of this invention carry from 0.5–5 mg/ml of taxol, thus allowing delivery of the drug in up to one one-hundredth or less of the volume now used without toxic cosolvents or cremophores.

Tumor-active analogs of taxol are known to the art and include analogs having acylated carbons of the taxene ring at the 7-position and 10-position.

Pharmaceutically acceptable oils are known to the art and include vegetable, flower, animal and marine oils.

The oil used for solubilizing taxol is preferably a marine oil, and more preferably, a deep-water marine oil. Oils having ether lipid as a major component thereof are preferred. Orange roughy oil, shark liver oil, squalene or squalane oil are preferred.

Dipole moment measurements of various oils are readily available in the literature, (e.g., McClellan, A. L. (1963), "Table of Experimental Dipole Moments," W. H. Freeman (publishers), San Francisco, Calif.; and Smith, J. W. (1955) "Electric Dipole Moments," Buttersworth Scientific Publications, London), and are experimentally determined by the method of oscillometry (Reilley, C. N. (1954), in *New Instrumental Methods in Electrochemistry*, P. Delahey (ed.), Interscience, New York, N.Y. pp. 319–345) or comparison to drug solubility (Gorman, W. G. and Hol G. D. (1964) Hol. J. Pharm. Sci. 53:1017).

The solutions of taxol or tumor-active analogs of taxol made by the methods of this invention are preferably used to prepare oil-in-water emulsions for pharmaceutical use in antitumor therapy. Emulsions are preferred vehicles for taxol for both intravenous and oral administration, and can be prepared by means known to the art using known surfactants from the solutions of taxol in oils of this invention. Surfactants useful in the preparation of such emulsions include, e.g., Pluronic F-86 ™ (BASF), polysorbate Tween 80 ™, those having HLB values between 10–13, and preferably Pluronic F-86.

This invention also includes self-emulsifying glasses prepared by the methods disclosed in abandoned U.S. Ser. No. 07/830,058, filed Feb. 3, 1992, incorporated herein by reference, and related applications. Such glass compositions comprise a water-soluble, nonsurface active matrix compound and an oil containing solubilized taxol or tumor-active taxol analog from which emulsions can be readily formed by contacting the glass with an aqueous phase.

No emulsive mixing or art-recognized surfactants are required to form emulsions from such self-emulsifying glasses. The matrix compounds are not surface active agents, surfactants or emulsifying agents. Among others, monosaccharides, disaccharides and nonsugar sweeteners such as cyclamates, saccharines and water soluble polymers including polyvinylpyrrolidones (PVP), cellulose derivatives, dextran, and maltodextrins function as matrix compounds in the formation of such self-emulsifying glasses. Saccharides including but not limited to sucrose, fructose and trehalose function as matrix compounds in the subject glasses. Preferred nonpolymeric matrix compounds are molecules which taste sweet, more preferred are molecules which are at least about as sweet as sucrose. Saccharides, monosaccharides, disaccharides, sugar alcohols and sugar derivatives, like chlorinated sugars, which are at least about as sweet as sucrose, are useful as matrix compounds. Nonsugar sweeteners useful as matrix compounds include various sweet tasting molecules including but not limited to amino acids, amino acid derivatives, Aspartame (Trademark) and derivatives thereof, and sulfamates including cyclamates, saccharines, acesulfams and derivatives thereof.

Polymeric matrix compounds that are useful in self-emulsifying glasses include among others, PVPs, dextran, maltodextrins and cellulose derivatives. Crosslinked and noncrosslinked PVPs ranging in molecular weight from about 15 to 70 thousand can be processed by the methods described herein to form self-emulsifying glasses. Water-soluble cellulose derivatives including carboxymethyl-cellulose and hydroxyalkycelluloses including hydroxmethyl- and hydroxypropylcelluloses can be processed by the methods described herein to form self-emulsifying glasses. Useful maltodextrins are dextrose copolymers with starch, classified as having dextrose equivalents from about 5 to about 25. Both agglomerated and nonagglomerated forms of maltodextrin function in such self-emulsifying glasses.

Molecules possessing a tripartite glucophore having the three structural features of a proton donor, an electronegative atom and a hydrophobic region are of particular use as matrix compounds in the preparation of self-emulsifying glasses, especially where water is the preferred solvent.

The tripartite glucophore is a structural feature associated with sweetness which consists of a polarizable bond, designated AH or A, an electronegative atom, designated B and a third feature. Initially two structural features: a proton donor or more generally a polarizable bond and an electronegative atom separated in space by about 2.5 to 4.0 Å were described as minimally required for sweet taste (Shallenberger and Acree (1967) Nature 216:480). Examples of AH include O-H groups, N—H groups and C—H groups of cycloalkyl groups or aromatic rings. Examples of B include oxygen atoms, oxime groups, nitro groups, carbonyl groups, and S—O or $SO_2$ groups. The AH, B unit in the cyclamate and saccharin sweeteners are assigned to the NH—$SO_2$ moieties. The third feature, designated X herein, is associated with increasing intensity of sweetness. The X feature is described specifically as a lipophilic region or hydrophobic bonding area (Deutsch and Hansch (1966) Nature 211:75), or more generally as a region capable of dispersive bonding or a region susceptible to electrophilic attack (Kier (1972) J. Pharmaceutical Sci. 61:1394–1397). Examples of the X feature include alkyl and alkenyl groups, cycloalkyl and cycloalkenyl groups, aromatic rings, and the C-2 substituent in aminonitrobenzenes. All three features are described as involved in binding of a sweet molecule to the taste receptor.

The features of the tripartite glucophore form a triangle with the AH-B distance ranging from about 2.5–4.0 Å, the AH-X distance ranging from about 3.1 to 5.2 Å and the B-X distance ranging from about 5.2 to 7.4 Å. The triangular tripartite glucophore structure is more narrowly depicted with an AH-B distance of about 2.6 Å, a B-X distance of about 5.5 Å and an X-AH distance of about 3.5 Å. Intensity of sweetness is associated with better fit or improved binding in the receptor. Sweet-tasting compounds which possess a tripartite glucophore, particularly in which the X feature is a region capable of hydrophobic bonding, are useful in the preparation of self-emulsifying glasses via the water solvent method as described herein. Those compounds possessing the tripartite glucophore which are sweeter than sucrose are preferred matrix compounds for use in the compositions and methods of the present invention.

The tripartite glucophore structure is found not only in sweet molecules, but also as a feature of the monomers which make up the polymeric matrix materials useful in this invention, such as PVP.

The weight ratio of matrix compound to oil phase in a self-emulsifying glass is more preferably between about 2:1 and 20:1 and most preferably between about 2:1 and 10:1.

The compositions of the present invention are also termed "inclusion compounds" herein. Matrix materials used herein may also be described in terms of their ability to form inclusion compounds or aggregates incorporating the oleaginous materials of this invention. Such matrix materials are capable of forming chains of indefinite length, either due to the fact that they are polymeric materials or by intermolecular hydrogen bonds in the presence of oil, such chains having surfaces that are relatively hydrophobic and surfaces that are relatively hydrophilic. The oleaginous material is enclosed within the cavities or interstices formed by lipophilic regions of the chains (Harata, K. and Vedaira, K. (1975) Bull. Chem. Soc. Jap. 48:375). When the solvent used to form the self-emulsifying glass is removed the matrix material forms a structure which "includes" the oleaginous material within it in discretely separated aggregates or small portions. The use of the word "compound" does not imply a definite stoichiometry. The molar ratio of oil to matrix may vary, as may the size of the matrix chains.

In general, the various matrix compounds can be admixed to form glasses of the present invention. Employing a mixture of matrix components can, for example, lead to self-emulsifying glasses with higher glass transition temperatures. The higher the glass transition temperature, the more kinetically stable the glass.

Glasses with higher glass transition temperatures will be generally more stable to storage and have longer shelf-lives. It is generally preferable that glass transition temperatures be about 20° C. or more above room temperature. Mixtures of nonpolymeric matrix compounds, such as sucrose, with polymeric matrix compounds, such as maltodextrin, result in glasses with higher transition temperatures compared to glasses formed with the nonpolymeric matrix compound alone. In particular, the use of a mixture of sucrose and maltodextrin as the matrix compound results in glasses having higher glass transition temperatures than sucrose-based glasses.

It is preferred in the subject self-emulsifying glasses that the weight ratio of the matrix compound to the oil phase is at least about 2:1.

Solutions of taxol or tumor-active taxol analogs in the pharmaceutically acceptable oils of this invention may be prepared by dissolving taxol crystals directly in the oil, preferably with the application of heat. More rapid dissolution is obtained by first dissolving the taxol in a more volatile, less viscous preliminary solvent such as anhydrous alcohol, e.g., ethanol or methanol. The primary solution is then mixed with an oil of this invention having a dipole moment of between about 0.5 and about 2.0 Debyes to form a second solution. This second solution may at this point be treated to remove the preliminary solvent, preferably by heating. Alternatively, the solvent may be removed later in the process as described below.

Solutions comprising taxol or a tumor-active taxol analog in a preferred oil can be emulsified by means known to the art to form pharmaceutical 10% w/v oil compositions having concentrations of the tumor-active ingredient of at least about 0.5 mg/ml up to about 5 mg/ml. Useful emulsions of this invention have concentrations of the tumor-active ingredient of about 3 mg/ml.

To avoid the use of surfactants which may be toxic or cause undesirable side-effects, it is preferred that such emulsions be produced using the self-emulsifying glasses described above.

Self-emulsifying glasses containing taxol and tumor-active taxol analogs are preferably prepared by combining the tumor-active ingredient and oil solution described above, with or without the presence of the preliminary solvent, with a nonsurface active matrix material, as defined above, and a sufficient amount of a solvent for the matrix material, such that substantially all of the matrix compound is dissolved to form a combination such that the combination is not a stable emulsion, followed by removing the solvent for the matrix compound, along with any preliminary solvent that may be present, from the combination such that a glass results.

The solvent for the matrix material employed can include but is not limited to water, aqueous solvents, aqueous alcohols, ethanol, methanol, and organic solvents in which the matrix compound is soluble, including among others, chloroform. Water and aqueous solvents including aqueous alcohols are preferred.

The matrix material and oil solution containing taxol or tumor-active taxol analog are preferably combined such that the weight ratio of the matrix compound to the oil solution is at least about 2:1. Solvent removal is preferably done by evaporation by application of a vacuum accompanied by nonvigorous mixing, i.e., nonemulsive mixing, most preferably by rotoevaporation. Solvent is removed until a dry-appearing solid, solid foam or film is produced. Rotoevaporation results in bubbling of the combination and the solid resulting from removal of solvent has the appearance of a solid foam. Substantially all the solvent is removed, leaving trace amounts of solvent, i.e., around 0.2 to about 0.5 percent.

The solid left after removal of substantially all the solvent is a glass. Glasses formed using nonpolymeric matrix compounds or mixtures of polymeric and non-polymeric matrix compounds often retain some level of short or medium range molecular order, designated microcrystallinity herein, as measured by differential scanning calorimetry (DSC). Glasses which are fully amorphous, as measured by X-ray diffraction and DSC can be prepared, but fully amorphous glasses may be very hygroscopic and the absorption of significant amounts of water into glasses is detrimental to their functionality and shelf-life. Thus, glasses retaining some level of microcrystallinity, from about 10% to 60% microcrystallinity as measured by DSC, are preferred. The subject glasses do not retain more than about 10% long range molecular order as measured by X-ray diffraction.

In the case in which a nonpolymer is employed as or in the matrix compound, it is preferred that the solvent be removed at a rate that is fast enough to prevent the formation of significant, i.e., greater than about 10%, long range molecular order via crystallization of the nonpolymer component of the matrix compound. This can generally be achieved if the rate of solvent removal is faster than the rate of crystallization of any matrix component from the solvent solution.

The process steps can in many cases be performed at about room temperature. It is preferred that the process steps are performed at the lowest temperatures possible which allow generation of a dry-appearing solid, still keeping the taxol or tumor-active taxol analog in solution. The process steps should be performed to avoid melting or decomposition of the matrix compound, i.e., the process should be performed at temperatures less than about the melting point or decomposition point of the matrix compound, generally about 140° C. or less.

Taxol is stable for at least about two hours at 130° C. Under vacuum taxol tends to precipitate from the oil solution at bath temperatures less than 50° to 60° C. Thus preferred temperatures for performing the process steps are about 60° C. to about 130° C.

If preliminary solvent is present, and if it is desired to remove it prior to adding matrix materials, preferred temperatures for removing the preliminary solvent from the taxol and oil solution are between about 60° C. and about 70° C., preferably about 60° C. This step is preferably done by heating under a nitrogen blanket for a sufficient period to remove substantially all the solvent, typically about 20 minutes.

The matrix material, preferably sucrose, is mixed with the taxol and oil solution, which may also contain preliminary solvent, at a preferred ratio of between about 2:1 and about 20:1::matrix:oil solution. The solvent for this composition, preferably water, is then added, preferably using the smallest amount of solvent which will dissolve the composition, i.e., about 2:1::solvent:matrix/oil phase. The solvent may be heated to aid in dissolution, preferably to about 80° C., for a sufficient period of time to dissolve the composition, i.e. about five minutes.

Solvent is then removed from the solubilized composition, preferably by rotoevaporation, under vacuum, preferably starting at about 500 mbar and increasing to maintain bubbling. The vapor temperature should be kept at about 30° C. or higher. When the vapor temperature no longer increases, usually after about half an hour, maximum vacuum is applied. The self-emulsifying glass is collected from the film or foam formed in the reaction vessel as a dry-appearing solid. The glass should be stored at room temperature at less than about 30% relative humidity.

A pharmaceutically effective emulsion containing taxol is produced from the self-emulsifying glass by mixing with sufficient aqueous phase, preferably an isotonic solution such as Normal Saline or 5% dextrose (D5W), to form an emulsion. No emulsive mixing or surfactants are necessary. The aqueous phase is added to the glass preferably at a ratio of between about 1 ml:1 g, and about 5 ml:1 g::aqueous phase:glass, to form a composition having a pharmaceutically-effective concentration of the tumor-active ingredient.

The emulsion so formed, after storage for several hours without agitation, has a particle size between about 5 μm and about 1 μm and remains stable at room temperature for periods of three weeks or more. Droplet size decreases over time. Droplet size of the emulsion as initially formed may be larger, e.g., between about 10 μm and about 2 μm.

For therapeutic use, emulsions containing between about 0.5 and about 5 mg/ml taxol or tumor-active taxol analog are prepared by the foregoing methods and administered orally or intravenously.

EXAMPLES

Example 1

Taxol (Sigma T-7402), 4.0 mg, was dissolved in anhydrous methanol. The taxol solution was added to 0.400 ml squalane oil (Sigma S-4510, lot 88F3528). The methanol was then removed with heating and nitrogen blanket at about 60° C. for 10 minutes. The taxol was completely solubilized in the squalane oil.

Example 2

The taxol-in-oil solution of Example 1 was added to 1.62 g of sucrose in a 100 ml vacuum flask. Sufficient water to just dissolve the sucrose was added to the flask and the mixture was heated to 80° C. in a rotary evaporator for approximately five minutes. Vacuum was applied to the flask at 500 mbar, and continually increased to maintain bubbling. Vapor temperature was maintained no lower than 30° C. When the vapor temperature no longer increased, after about 30 minutes, maximum vacuum was applied and the flask lifted out of the water bath. The self-emulsifying glass product in the form of a foam was collected from the flask. The glass had a moisture content of less than or equal to 0.1% to less than or equal to 0.29%.

Example 3

The self-emulsifying glass of Example 2 was added to 0.8 ml normal saline and gently swirled by hand to produce an oil-in-water emulsion comprising taxol in the oil phase. Droplet size was measured at about 2–10 μm.

Example 4

The emulsion Example 3 was tested for therapeutic activity as follows:

Twelve mice weighing 14 to 25 grams, strain A/J (lung tumor model as described in Malkinson, A. M. (1920 Cancer Res. (suppl.) 52:2670s–2676s), in which urethane-induced lung tumors, at an average of 30 per mouse after 14 weeks of treatment, are treated with the emulsion of Example 3 for a dosage of 5 mg/kg taxol. The emulsion is administered by bolus i.v. Treatment cycle is repeated four times. Controls using identical procedures and an equivalent oil/sucrose glass emulsion free of taxol are performed. At the end of the study tumor number in the rats treated with the formulation of this invention decreases significantly compared to controls.

I claim:

1. A composition of matter comprising a pharmaceutically effective amount of taxol or a tumor-active analog thereof, completely solubilized in a squalene or squalane oil.

2. The composition of matter of claim 1 comprising a pharmaceutically effective amount of taxol completely solubilized in said squalene or squalane oil.

3. The composition of matter of claim 2 which contains at least about 0.5 mg/ml taxol.

4. The composition of matter of claim 3 in emulsion form.

5. The emulsion of claim 4 which does not contain a surfactant.

6. A composition of matter consisting essentially of a pharmaceutically effective amount of taxol completely solubilized in a squalene or squalane oil.

7. The composition of matter of claim 6 containing about 10 mg/ml of taxol.

8. A method for solubilizing taxol or a tumor-active taxol analog in a pharmaceutically acceptable carrier which is a squalene or squalane oil comprising the steps of:
   (a) solubilizing taxol or said taxol analog in an anhydrous alcohol;
   (b) mixing the alcohol solution of (a) with a sufficient amount of said pharmaceutically acceptable carrier to solubilize said alcohol solution therein; and
   (c) removing said anhydrous alcohol from said carrier solution formed in step (b) by rotary evaporation thereby resulting in a carrier solution in which said taxol or taxol analog is completely solubilized in said squalene or squalane oil.

* * * * *